United States Patent [19]
Collett

[11] Patent Number: 5,279,577
[45] Date of Patent: Jan. 18, 1994

[54] HYPODERMIC UNCAPPING AND RECAPPING APPLIANCE AND METHOD

[76] Inventor: Kenneth R. Collett, 11889 Fiddler Dr., Boise, Id. 83704

[21] Appl. No.: 867,758

[22] Filed: Apr. 13, 1992

[51] Int. Cl.$^5$ ............................................. A61M 5/32
[52] U.S. Cl. ................................. 604/192; 604/263; 128/919; 206/365; 248/176
[58] Field of Search ............... 604/192, 263, 110; 128/919, 765, 764; 206/364-366; 284/172, 316.2

[56] References Cited

U.S. PATENT DOCUMENTS

| | | | |
|---|---|---|---|
| 3,210,816 | 10/1965 | Clemons | 604/174 X |
| 4,830,319 | 5/1989 | Willoughby | 248/176 |
| 4,844,249 | 7/1989 | Coulombe | 604/438 |
| 4,846,803 | 7/1989 | Emerson | 604/263 |
| 4,915,698 | 4/1990 | Levenson | 604/192 |
| 4,919,656 | 4/1990 | Bracker et al. | 604/192 |
| 4,921,199 | 5/1990 | Villaveces | 248/314 |
| 4,950,015 | 8/1990 | Nejib et al. | 294/19.1 |
| 4,955,865 | 9/1990 | Steiner et al. | 604/192 |
| 4,979,945 | 12/1990 | Wade et al. | 604/192 |
| 4,981,476 | 1/1991 | Aichlmayr et al. | 604/192 |
| 4,984,686 | 1/1991 | Shillington | 206/366 |
| 4,986,817 | 1/1991 | Code | 604/192 |
| 4,995,870 | 2/1991 | Baskas | 604/110 |
| 5,007,535 | 4/1991 | Meseke et al. | 206/366 |
| 5,013,299 | 5/1991 | Clark | 604/114 |
| 5,024,326 | 6/1991 | Sandel et al. | 206/366 |
| 5,024,666 | 6/1991 | Pituch | 604/263 |
| 5,037,400 | 8/1991 | Curry | 604/192 |

Primary Examiner—John D. Yasko
Assistant Examiner—Mark O. Polutta
Attorney, Agent, or Firm—Frank J. Dykas; Craig M. Korfanta; Ken J. Pedersen

[57] ABSTRACT

A hypodermic appliance for facilitating a one-handed uncapping and recapping of hypodermic apparatus and the like. An appliance separate from the hypodermic apparatus includes an elongated tapered opening in a plate through which a needle-covering sheath of a hypodermic apparatus is placed. The tip of the sheath abuts a tip holder which provides a fulcrum point for rocking the hypodermic apparatus from the wider portion of the opening to the narrower portion of the opening and vice-versa. The sides of the sheath are gripped in the narrower portion of the opening, whereupon the needle may be withdrawn from the sheath leaving the sheath lodged in the appliance. After using the hypodermic apparatus, the needle is reinserted by the use of only one hand into the sheath, and then the capped hypodermic apparatus is rocked to the wider portion of the opening and withdrawn from the appliance.

13 Claims, 2 Drawing Sheets

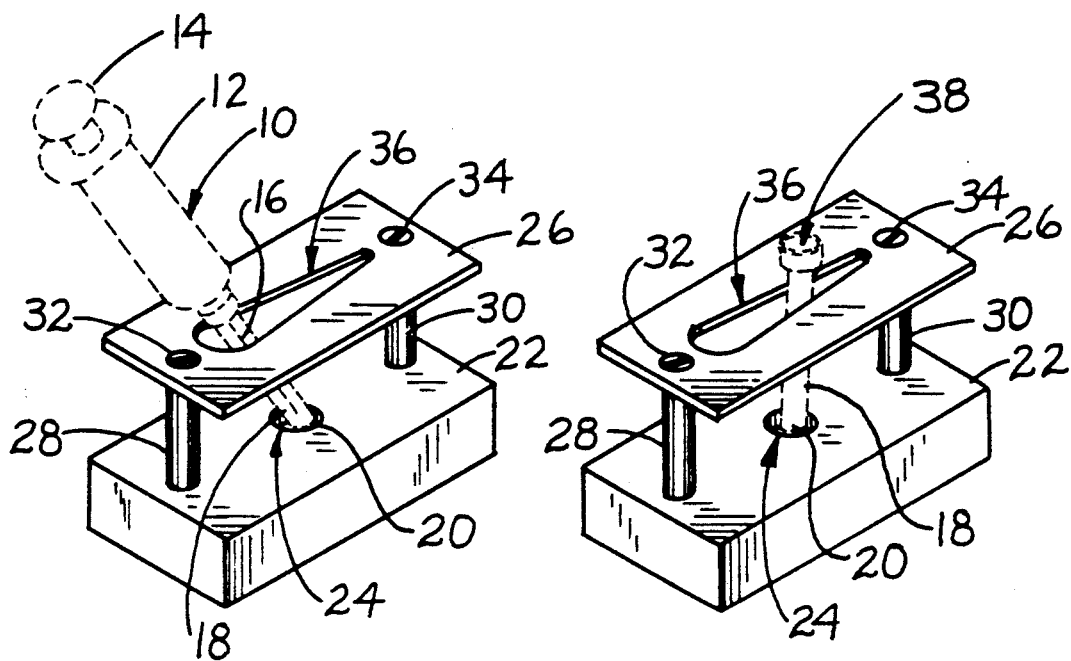
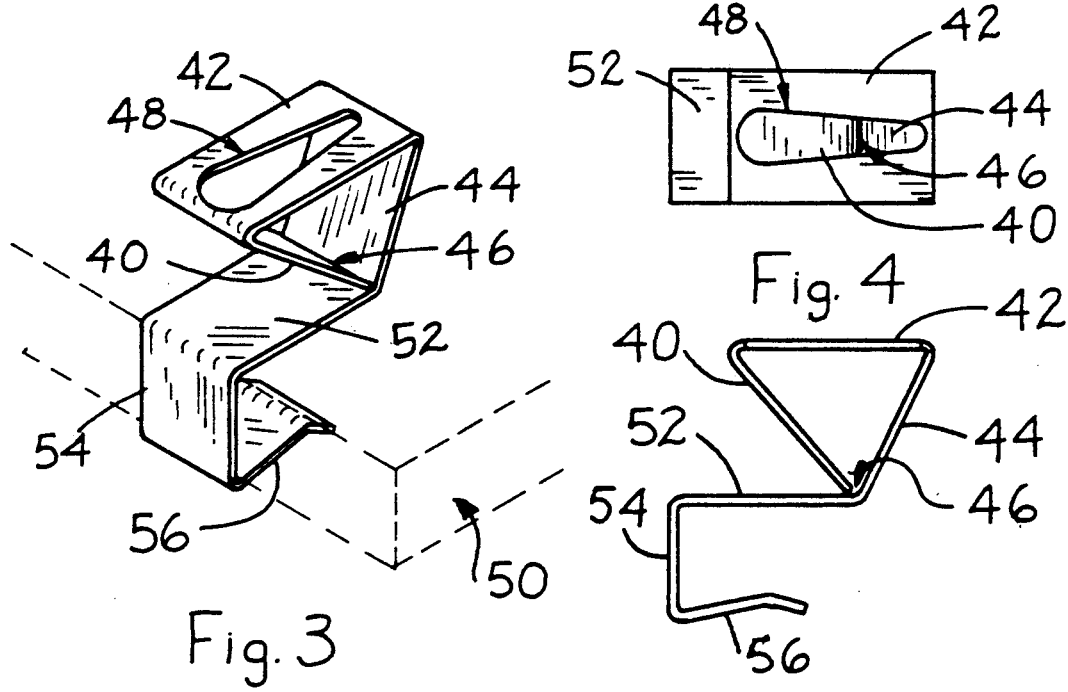

HYPODERMIC UNCAPPING AND RECAPPING APPLIANCE AND METHOD

BACKGROUND OF THE INVENTION

This invention relates to medical appliances, and in particular to a device for use in conjunction with hypodermic apparatus, or the like, in which a needle is covered by a sheath for the purposes of safety and sterility when the needle is not in use, the invention being an appliance, separate from the hypodermic apparatus, which assists the medical professional in one-handedly removing the sheath from the needle and, after using the hypodermic apparatus, one-handedly replacing the needle into the sheath.

In the past it has been the practice of medical professionals to use hypodermic apparatus such as syringes, I.V.'s, and the like which have a sharp hollow needle for penetrating the skin. In recent times it has become the practice in countries with advanced medical facilities to use disposable hypodermic apparatus. For the purpose of sterility the needles of such apparatus are supplied with a removable cap or sheath. The sheath is most commonly an elongated plastic part having a cavity for receiving the needle in a mouth thereof, and being attachable to the body of the hypodermic needle assembly by friction. The needle is withdrawn from the sheath just prior to the use of the hypodermic apparatus.

More recently, it has become advisable to replace the needle into the sheath after it has been used in order to help prevent needle-stick injuries which can transmit disease to any person other than the original patient. It is the practice in most medical institutions to dispose of sharp instruments into a special container where they cannot easily inflict injury to others. However, as an added precaution it is becoming a wise policy to make sure that the hypodermic needles are reinserted into their sheaths immediately after each use so that there is a substantially decreased possibility that a needle-stick injury might occur. This is a primary concern of medical workers and their employers because of the seriousness of diseases which can be transferred accidently in this manner.

New hypodermic apparatus are being developed in which the needle is not exposed or becomes automatically covered upon withdrawing the needle from the patient. However, these devices are not readily available to the medical community, are more complex in structure, cost more to manufacture, and are prone to malfunction. Unless and until such devices become universally used the problem of potential needle-stick injuries remains.

Also, there have been developed some devices which allow medical professionals to recap the hypodermic needle with the sheath after use. However, these devices generally require the use of both hands. This is unacceptable to the medical community because of the possibility of sticking the needle into the other hand when trying to recap it.

Some devices which do not require the use of both hands have been developed. However, those devices of which the applicant is aware are fairly complex and costly. Moreover, they are generally designed to be sat upon a table and as such are not readily positioned where they are most convenient for use. Another drawback to known devices is that they are not readily able to be sterilized.

Accordingly, it is the object of the present invention to provide an accessory or appliance, separate from the hypodermic apparatus, to assist medical professionals in one-handedly uncapping and recapping hypodermic apparatus.

Another object is to provide such an appliance which is simple to manufacture, and of relatively low cost, and yet is easily useable and can be readily available near the patient.

A further object is to provide an appliance which is readily replaceable and/or which can be sterilized.

These and other objects and advantages of the present invention and the manner in which they are achieved will become apparent in the following specification and claims.

SUMMARY OF THE INVENTION

In its basic concept the present invention is a device or appliance for uncapping and recapping a hypodermic apparatus, including a plate having a varying width elongated opening therein and a sheath tip holder mounted a spaced distance from the plate and forming a fulcrum point for the tip of the sheath. The opening in the plate is configured and dimensioned to allow the nose of the sheath to be placed through the wider portion thereof and the tip of the sheath to abut the tip holder. The narrower portion of the opening in the plate is configured and dimensioned to grasp the sides of the sheath when the sheath is rocked about the fulcrum point toward the narrower part of the opening. This causes the sheath to become lodged in the uncapping-/recapping appliance, and the needle may then be withdrawn from the sheath for use, using only one hand. After use, or when it is no longer advisable to have the needle exposed, the needle is recapped by placing the needle into the sheath as it is held by the uncapping-/recapping appliance. Importantly, this is also a one-hand-only operation. The hypodermic apparatus, including the sheath, may then be removed by rocking the apparatus about the fulcrum point toward the wider portion of the opening in the plate and then withdrawing it from the appliance.

BRIEF DESCRIPTION OF THE DRAWINGS

FIG. 1 is a top perspective view of a hypodermic uncapping and recapping appliance of the present invention, shown together with a hypodermic apparatus including a needle-covering sheath stationed in a first position relative to the uncapping and recapping appliance.

FIG. 2 is a top perspective view of the appliance of FIG. 1, shown together with the sheath stationed in a second position relative to the uncapping and recapping appliance.

FIG. 3 is a top perspective view of a second embodiment of the hypodermic uncapping and recapping appliance of the present invention.

FIG. 4 is a top view of the appliance of FIG. 3.

FIG. 5 is a side view of the appliance of FIG. 3.

DESCRIPTION OF THE PREFERRED EMBODIMENTS

Figure 6:
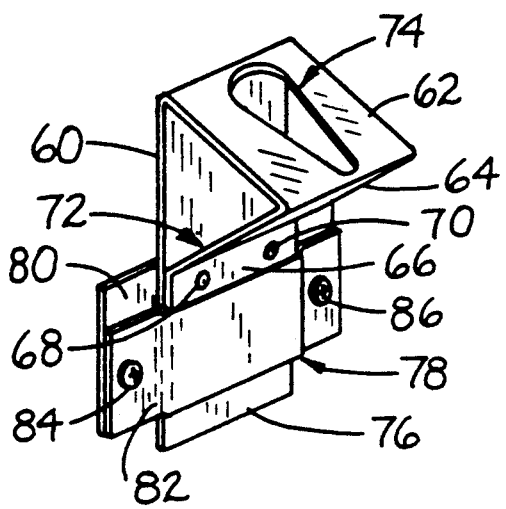
FIG. 6 is a top perspective view of a third embodiment of the hypodermic uncapping and recapping appliance of the present invention.

As shown in FIG. 1, the hypodermic uncapping and recapping appliance of the present invention is used in conjunction with a hypodermic apparatus, or the like, such as a hypodermic syringe shown generally in dashed lines at 10. In basic description, the syringe includes a body 12, a plunger 14, a hollow needle 16, and a sheath 18 which covers the needle and fits onto the syringe body by friction. The nose or tip of the sheath is denoted at 20. This type of syringe is well known in the art and is only an example of one type of hypodermic apparatus which may be used in conjunction with the present invention.

The hypodermic uncapping and recapping appliance of the present invention is a device separate from the hypodermic apparatus and includes a base 22 which has an indentation 24 therein that serves as a tip holder for the tip 20 of the hypodermic apparatus 10. A plate 26 is supported in spaced relationship to the tip holder by standoffs 28 and 30, and secured by screws 32 and 34. An elongated opening 36 in the plate is configured and dimensioned to have a varying width such that sheath 18 may be placed through the wider portion thereof. In this embodiment the opening is a closed-end, V-shaped slot, rounded at the ends. The tip 20 of the sheath may be placed in tip holder indentation 24 which includes means, such as the sides of the indentation, to provide a fulcrum point for rocking the hypodermic apparatus back and forth from the wider portion of the opening to the narrower portion of the opening, and vice-versa.

FIG. 2 illustrates the sheath 18 of the hypodermic apparatus 10 lodged in the narrower portion of opening 36 in plate 26. The edges of the opening may be beveled in order to more firmly grip the sides of the sheath. In this position the needle 16 of the hypodermic apparatus may be withdrawn from the sheath for use. The sheath remains lodged in the uncapping and recapping appliance. After the hypodermic apparatus is used the needle may be returned to the sheath by a one-handed operation in which the needle is placed into the mouth 38 of the sheath and the hypodermic apparatus is pushed forwardly into the sheath until the sheath is once again tightly friction fitted onto the body 12 of the hypodermic apparatus. Rocking the hypodermic apparatus toward the wider portion of the opening frees the sheath from the grip of the appliance, and the capped hypodermic apparatus may then be removed. It is to be noted that the tip holder may be formed by various means other than indentation 24. The purpose thereof is to provide means for a fulcrum point for abutment by the tip 20 of the sheath, about which the hypodermic apparatus may pivot forwardly and rearwardly in the direction of the opening. Any means to substantially accomplish this falls within the scope intended herein. Likewise, the opening may be of various shapes without departing from the spirit or scope of the invention. The relative position of the tip holder to the opening in the plate is also a matter of considerable latitude so long as the distance or position does not exceed the limits of the length of the sheath. Also to be noted is that, as shown in FIG. 2, the sheath need not engage the most narrow part of the opening, but only a narrower portion relative to the position wherein the sheath readily passes through the opening. The hypodermic uncapping and recapping appliance of the present invention is quite universal in regards to its being useable with variously dimensioned hypodermic apparatus sheaths. The appliance will accept any diameter sheath up to the maximum width of the opening. The length of the sheath is also non-critical. So long as the sheath is able to extend through the opening and abut the tip holder the appliance will function. Since the appliance grips the sides of the sheath the longitudinal position of the point of contact of the sheath with the plate is not important. Thus, widely varying hypodermic apparatus sizes are accommodated by the appliance of the present invention.

FIGS. 3, 4 and 5 illustrate a second embodiment of the hypodermic uncapping and recapping appliance of the present invention. In this embodiment the device is formed by a single piece of strip material bent or configured into a substantially triangular shape. A first leg 40 extends angularly upwardly, and folds into a second leg 42 which is substantially horizontal. The second leg folds to a third leg 44 which extends angularly downwardly to a point substantially adjacent to the starting point of the first leg, thereby forming a triangular piece of strip material. The lower vertex 46, formed by the angled intersection of the adjacent first and third legs, forms one angle of a triangle, it being the tip holder, and providing similar function to indentation 24 of the previous embodiment. Leg 42, being the side opposite the lower vertex, is the plate in which is located a V-shaped varying width opening 48. FIG. 4 illustrates in plan view the opening. A hypodermic apparatus such as the one illustrated at 10, which includes a needle-covering sheath 18, may be used in this second embodiment similarly to the use of the first embodiment. The sheath of the hypodermic apparatus may be placed through the opening in the wider portion thereof until its tip contacts the tip holder formed by the legs at vertex 46. The tip holder provides a fulcrum point about which the hypodermic assembly may be rocked in the elongated direction of the opening. Since there is no side to side movement there is not a requirement that the tip holder have side walls. In this embodiment the strip material continues from the bottom of leg 44 to once again be bent to form a mounting means for securing the device to a solid mounting structure such as a table top, illustrated in dashed lines generally at 50. The mounting means comprises a spring clip formed from the strip material by a horizontal leg 52, being bent into a vertical leg 54 and then into a dog-leg shaped piece 56. Horizontal leg 52 rests on a table top, while dog-leg 56 holds the device in place by a spring action pressing against the bottom of tabletop 50.

FIG. 6 illustrates a third embodiment of the present invention. In this embodiment the hypodermic uncapping and recapping appliance is constructed from a piece of strip material in much the same manner as the second embodiment. A first leg 60, second leg 62 and third leg 64 are arranged in a triangular form. For the purpose of rigidity a tab 66, which is a piece of the strip material bent from leg 64, is fastened to leg 60 as by spot welds 68 and 70. A lower vertex, forming a tip holder 72 is formed between legs 60 and 64. Opposite the angle which forms the tip holder, leg 62 forms the plate having an elongated tapered opening 74 therein. Mounting means is provided for attaching the device to a solid surface such as a wall (not shown). This includes a blade 76, formed out of the strip material continuous with leg 60. A bracket, shown generally at 78, includes a back plate 80 and a front plate 82 fastened to the wall by screws 84 and 86. The front plate is curved outwardly, forming a pocket for insertion of the blade. Thus the appliance is able to be removed from the bracket by sliding it upwardly. This is a very useful feature because it allows the appliance to be subjected to sterilization. It will be noted that in this embodiment the hypodermic apparatus when placed through the opening and having the tip abutting the fulcrum point, leans away from the wall to provide easy and convenient access thereto.

Figure 7:
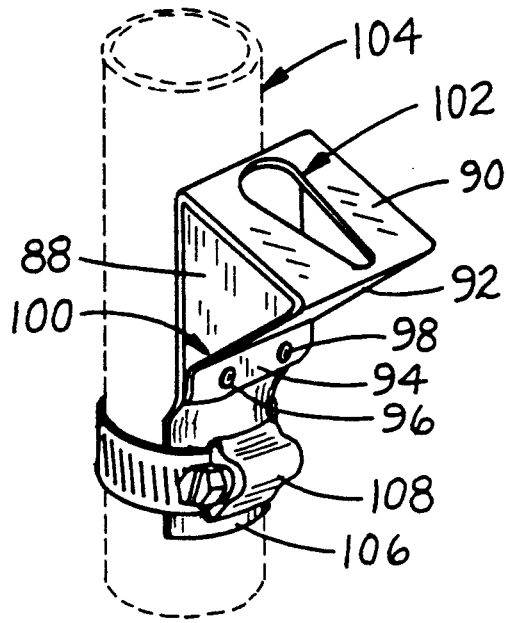
FIG. 7 is a top perspective view of a fourth embodiment of the hypodermic uncapping and recapping appliance of the present invention.

FIG. 7 illustrates a fourth embodiment of the present invention, wherein the hypodermic uncapping and recapping appliance is constructed from a piece of strip material in much the same manner as the second and third embodiments. A first leg 88, a second leg 90, and a third leg 92 are arranged in triangular form. For the purpose of rigidity tab 94, which is a piece of the strip material bent from leg 92, is fastened to leg 88 as by spot welds 96 and 98. A lower vertex, forming a tip holder 100 is formed between legs 88 and 92. Opposite the angle that forms the tip holder, leg 90 forms the plate having an elongated tapered opening 102 therein. This embodiment includes mounting means specifically designed for attachment to an upright pole 104. A blade 106 is formed out of the strip material continuous with leg 88. The blade is curved to conform with the surface of the pole. A clamp 108, or the like, secures the appliance to the pole. A pole such as described may be part of an I.V. stand, or the like, which puts the appliance in useful proximity to the patient.

Figure 8:
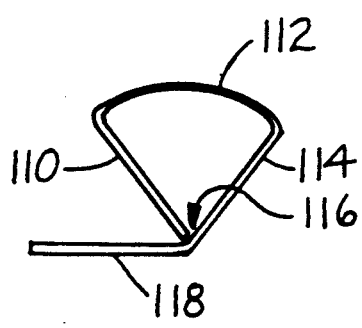
FIG. 8 is a side view, similar to FIG. 5, of a fifth embodiment of the hypodermic uncapping and recapping appliance of the present invention.

FIG. 8 illustrates a fifth embodiment of the present invention. In this embodiment the hypodermic uncapping and recapping appliance is constructed from a piece of strip material in somewhat the same manner as the previous embodiments. FIG. 8 illustrates only a side view of the device but it is to be understood that it is of similar construction and relative dimension as previously shown. A first leg 110, a second leg 112, and a third leg 114 are arranged in a somewhat triangular form. A tip holder 116 is formed at the vertex of legs 110 and 114, and provides a fulcrum point about which the tip 20 of sheath 18 is pivoted. Leg 112 forms a plate which is substantially arcuate in a radius about the fulcrum point thus providing a constant dimension from the fulcrum point to plate 112. The plate includes an elongated opening of varying width (not shown) similar to the previous embodiments. Consequently, the sides of the opening tend to engage the sheath at the same distance from its tip regardless of the diameter of the sheath. This feature is especially important for syringes with short and/or small diameter sheaths. A blade 118 is formed of the same strip material and folds from leg 114 to form a horizontally extending means for attachment. The blade may engage with a bracket similar to bracket 78 were the bracket mounted on a flat surface such as a tabletop or the like. This illustrates that the mounting means may be bent to any appropriate angle to fasten the appliance to any desired solid mounting structure.

Figure 9:
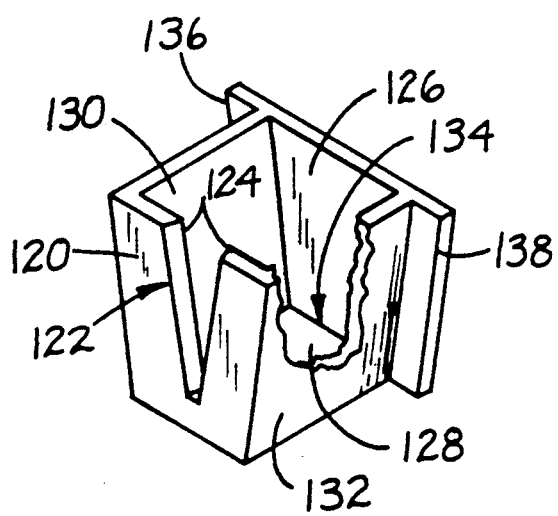
FIG. 9 is a top perspective view of a sixth embodiment of the hypodermic uncapping and recapping appliance of the present invention.

FIG. 9 illustrates a sixth embodiment of the hypodermic uncapping and recapping appliance of the present invention. This embodiment is configured such that it could be manufactured as a plastic injection molded part or the like. A plate 120 stands vertically and has a varying width opening 122 therein. The opening is unclosed at its widest part and is configured and dimensioned such that a sheath 18 of a hypodermic apparatus can be placed through the wider portion thereof. The edges of the opening are beveled as shown at 124 to aid in gripping the sheath. It is apparent from this embodiment that the appliance need not have an enclosed opening to properly grasp the sheath. The remainder of the structure forms a box, having a back wall 126, a bottom 128 and sides 130 and 132. Part of side 132 is shown broken away in order to illustrate that bottom 128 and back 126 form a tip holder providing a fulcrum point 134 at the inside edge between the bottom and back walls of the box against which the tip 20 of the sheath of a hypodermic apparatus abuts. Because the sheath engages the appliance at a downwardly projecting angle, the tip of the sheath does not have a tendency to slide upwardly as the sheath is seated in the appliance. The back wall extends past the sides forming wings 136 and 138. The wings are useful in providing a mounting means for securing the appliance to a solid mounting surface. The entire assembly is tapered so that the top is wider than the bottom. This facilitates mounting the appliance and provides a narrow bottom for the fulcrum point so that the side walls prevent lateral shifting of the tip of the sheath, as well as facilitating the manufacture of the device.

OPERATION

The purpose of the hypodermic uncapping and recapping appliance of the present invention is to facilitate the safety of medical personnel during the procedure of using a hypodermic apparatus, or the like, to prevent needle-stick injuries. For example, a hypodermic syringe having a needle-covering sheath is inserted into the uncapping and recapping device of the present invention by placing the sheath with the needle inside through the wider portion of the opening in the plate and engaging the tip holder with the tip of the sheath. The hypodermic apparatus is then rocked about the fulcrum point so that the sheath contacts the plate at a narrower portion of the opening. This causes the sheath to become lodged in the tapered opening. The needle is then withdrawn from the sheath for use, leaving the sheath in the uncapping and recapping device. Upon completing use of the needle, the needle is reinserted back into the sheath with the use of only one hand. The hypodermic apparatus is then rocked about the fulcrum point so that the sheath is in the wider portion of the opening. At this point the sheathed hypodermic apparatus may be withdrawn from the uncapping and recapping device.

Having described my invention in its preferred embodiments, I claim:

1. A recapping device for removably receiving a hypodermic apparatus having a needle and a needle-covering sheath, said sheath having sides, a first, mouth end for removably receiving the needle of the hypodermic apparatus, and a second, nose end culminating at a top for covering the needle, said sheath being removably attached to the hypodermic apparatus by friction, said recapping device consisting of:

(a) a plate having an elongated, varying width opening therein, with a first, wider portion and a second, narrower portion, the wider portion of the opening being configured and dimensioned to let the needle-covering sheath readily pass through, and the narrower portion of the opening being configured and dimensioned to engage and grasp the sides of the sheath;

(b) a tip holder attached to the plate and mounted in spaced apart relation thereto for receiving the tip of the sheath and having means therein to provide a fulcrum point for the tip for rocking the hypodermic apparatus back and forth from the wider portion of the opening to the narrower portion of the opening, and vice-versa;

(c) means for attaching the tip holder to the plate, and for supporting and securing them in relative, spaced-apart relationship; and (d) means for mounting said recapping device to a solid mounting structure.

2. The recapping device of claim 1 wherein the plate is arcuate in a radius about the fulcrum point.

3. The recapping device of claim 1 wherein the opening is a closed-end, V-shaped slot, rounded at the ends.

4. The recapping device of claim 1 wherein the opening is an unclosed, V-shaped slot.

5. The recapping device of claim 1 wherein the tip holder is an indentation in a base beneath the plate.

6. The recapping device of claim 1 wherein the tip holder is a vertex at an angled intersection in the means for attaching the tip holder to the plate.

7. The recapping device of claim 1 wherein the tip holder is an inside edge between the bottom and back walls of a box.

8. The recapping device of claim 1 where the mounting means comprises a spring clip.

9. The recapping device of claim 1 wherein the mounting means comprises a flat blade and a bracket means.

10. The recapping device of claim 1 wherein the mounting means comprises a curved blade and a clamp means.

11. The recapping device of claim 1 wherein the plate, tip holder, means for attaching the tip holder to the plate and at least part of the means for mounting the recapping device are formed from a single piece of strip material.

12. The recapping device of claim 11 wherein the plate, tip holder and means for attaching the tip holder to the plate are bent from the single piece of configured into a substantially triangular shape from a side view.

13. A method of one-handedly uncapping and recapping a hypodermic apparatus having a needle and a needle-covering sheath, said sheath having sides, a first, mouth end for removably receiving the needle, and a second, nose end culminating at a tip for covering the needle, said sheath being removably attached to the hypodermic apparatus by friction, said method of uncapping and recapping consisting of:

(a) inserting the nose end of the sheath attached to the hypodermic apparatus into an elongated, varying-width opening in a plate, said opening having a first, wider portion and a second, narrower portion, at the wider portion thereof;

(b) engaging the tip of the sheath in a tip holder attached to the plate and mounted in spaced-apart relation thereto, said tip holder having means therein to provide a fulcrum point for the tip for rocking the hypodermic apparatus back and forth from the wider portion of the opening to the narrower portion of the opening, and vice-versa;

(c) rocking the hypodermic apparatus about the fulcrum point from the wider portion of the opening to the narrower portion of the opening so that the narrower portion of the opening engages and grasps the sides of the sheath;

(d) disengaging the hypodermic apparatus from the needle-covering sheath, and withdrawing the needle from the mouth end of the sheath for use, leaving the sheath grasped in the narrower portion of the opening in the uncapping and recapping device;

(e) after use of the needle, inserting it back into the mouth end of the sheath, and engaging the hypodermic apparatus with the sheath;

(f) rocking the hypodermic apparatus about the fulcrum point from the narrower portion of the opening to the wider portion of the opening, so that the narrower portion of the opening disengages from the sides of the sheath; and (g) withdrawing the hypodermic apparatus from the wider portion of the opening of the uncapping and recapping device with the sheath attached.

* * * * *